(12) United States Patent
Patterson et al.

(10) Patent No.: US 9,244,024 B1
(45) Date of Patent: Jan. 26, 2016

(54) APPARATUS AND METHOD FOR DIGITAL RADIOGRAPHIC INSPECTION OF PIPES

(71) Applicant: IHI Southwest Technologies, Inc., San Antonio, TX (US)

(72) Inventors: Robert Brice Patterson, San Antonio, TX (US); Duncan J. Maclean, Helotes, TX (US)

(73) Assignee: IHI Southwest Technologies, Inc., San Antonio, TX (US)

( * ) Notice: Subject to any disclaimer, the term of this patent is extended or adjusted under 35 U.S.C. 154(b) by 62 days.

(21) Appl. No.: 14/449,271

(22) Filed: Aug. 1, 2014

(51) Int. Cl.
*G01N 23/02* (2006.01)
*G01N 23/18* (2006.01)
*G21K 1/02* (2006.01)

(52) U.S. Cl.
CPC ............... *G01N 23/18* (2013.01); *G21K 1/025* (2013.01)

(58) Field of Classification Search
CPC ............ G01N 23/04; G01N 2223/419; G01N 23/046; G01N 2223/628; G01N 23/18; G01N 2223/076; G01N 23/223; G01N 2223/601; G01N 23/203; G01N 9/24; G01N 2223/1013; G01N 2223/205; G01N 2223/612; G01N 2223/637; G01N 23/00; G01N 2223/3303; G01N 2223/3304; G01N 2223/629; G01N 23/02; G01N 23/12; G01N 23/20; G01N 23/20016; G01B 15/025; G01B 15/045; B23K 31/12
USPC .................................................. 378/57, 58, 62
See application file for complete search history.

(56) References Cited

U.S. PATENT DOCUMENTS

| | | | | |
|---|---|---|---|---|
| 4,725,963 A | * | 2/1988 | Taylor | G01N 23/18 378/20 |
| 5,614,720 A | * | 3/1997 | Morgan | G01N 23/18 250/358.1 |
| 6,137,860 A | * | 10/2000 | Ellegood | B24B 7/005 228/104 |
| 2012/0201347 A1 | | 8/2012 | Prentice et al. | |

* cited by examiner

*Primary Examiner* — Irakli Kiknadze
(74) *Attorney, Agent, or Firm* — Gunn, Lee & Cave, P.C.

(57) ABSTRACT

A digital radiographic tool with drive car for moving along track sections attached longitudinally to a pipe is shown. The drive car carries (1) a collimator on one side of the pipe for projecting x-rays or gamma rays on said pipe and (2) a linear digital array on an opposing side of the pipe for collecting x-rays or gamma rays that have passed through the pipe. The collected rays are processed to indicate any defects in the pipe. The digital radiographic tool is adjustable to allow inspection of pipes that have obstructions adjacent thereto.

20 Claims, 11 Drawing Sheets

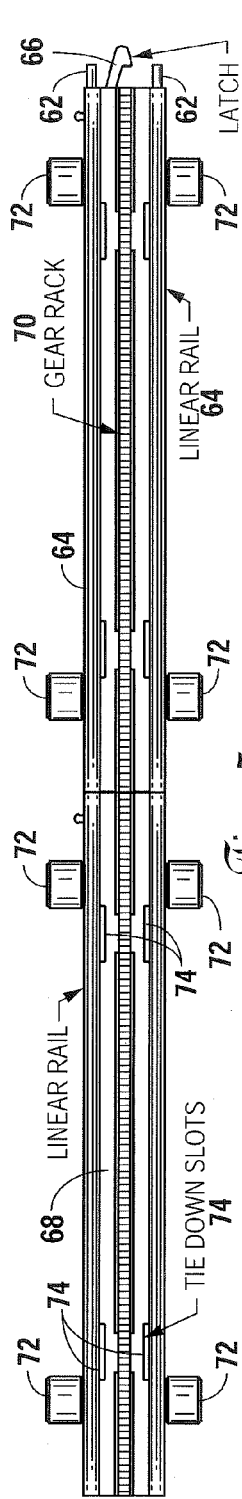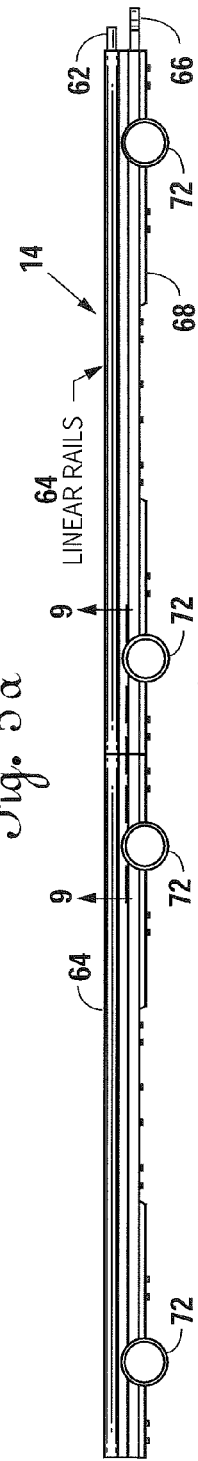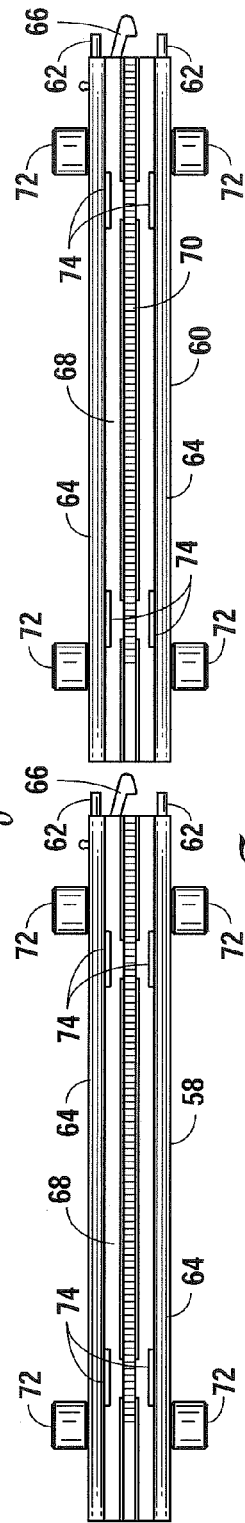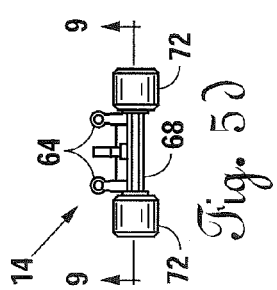

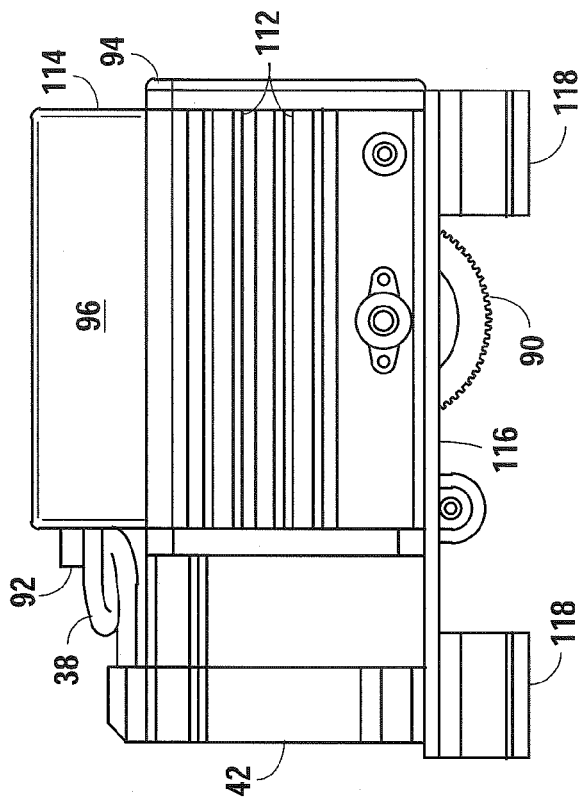
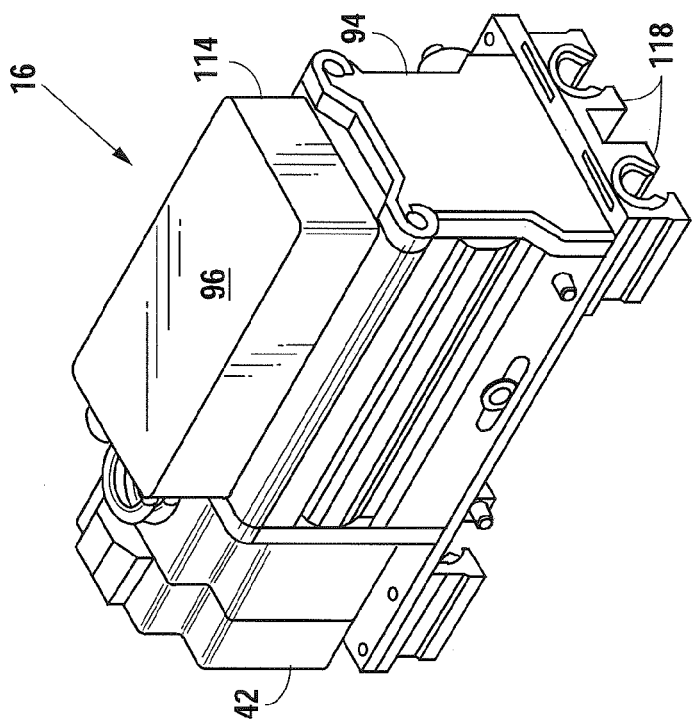
Fig. 6b
Fig. 6a

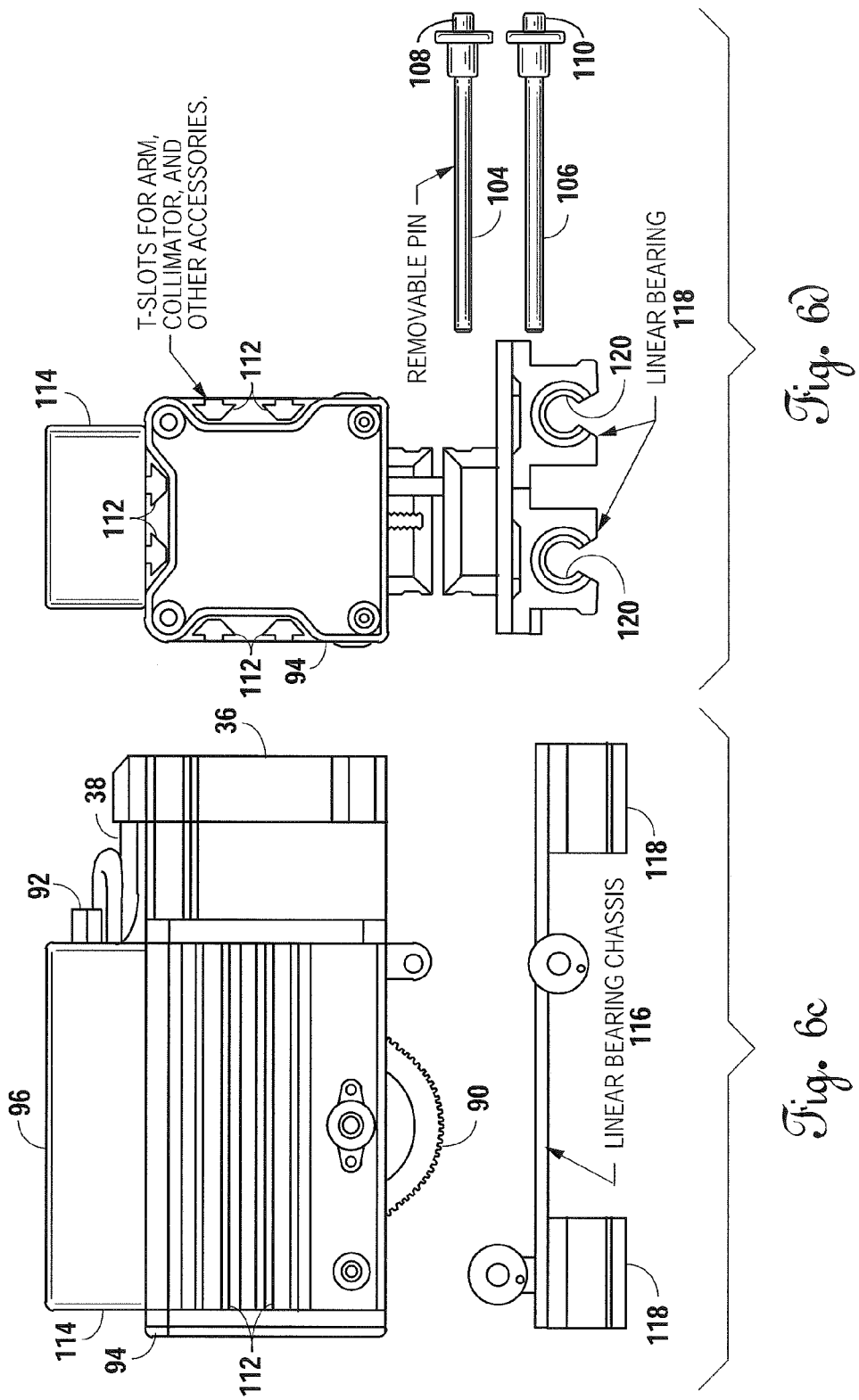

APPARATUS AND METHOD FOR DIGITAL RADIOGRAPHIC INSPECTION OF PIPES

FIELD OF THE INVENTION

The present invention relates to the inspection of pipes, and more particularly, to a device and/or method of using x-rays or gamma rays transmitted through a pipe and collected on the other side of the pipe in a digital detector array to determine if there are defects in the pipe.

BACKGROUND OF THE INVENTION

Pipelines are commonly used to transport material such as gas, oil, slurry or similar substances over long distances. Such pipelines are normally made out of metal and are commonly joined together with welds. In refineries, pipelines are used to transport material from one portion of the refinery to another. The pipeline may (or may not) be covered with insulation.

Such pipelines may corrode and, if the corrosion is not detected early enough, the pipelines may start to leak. If the leak is not detected early, catastrophic results may occur, including fires and/or explosions. Preferably, the corrosion is detected before a leak ever occurs.

Non-destructive testing, including the use of x-rays or gamma rays penetrating the pipeline, is used to determine if a pipeline has defects therein as may typically be caused by corrosion. U.S. Patent Publication No. US 2012/0201347 A1, published on Aug. 9, 2012 by Prentice et al. and assigned to Shawcore Ltd. shows a method and apparatus for inspecting pipelines to determine if there are any defects in a pipeline. However, the Prentice patent is difficult to install and requires access to the entire circumference of the pipeline. If a pipeline is in a refinery and is supported on support beams, the Prentice invention cannot inspect the pipe where the pipe touches the support beam.

In pipelines, if the pipeline is buried, non-destructive testing of the buried pipeline is normally made by sending a pig through the pipeline. The pig is typically made up of (a) a drive package, (b) a flux loop that does the sensing and (c) a recorder package. Using such a pig, the entire Trans Alaska Crude Oil Pipeline was tested in 1997. However, for many pipelines, especially in refineries or processing plants, a pig cannot be run through the pipeline. Also, many of the pipelines are covered with insulated material which prevents direct access to the pipeline.

The purpose of the non-destructive testing is to use a non-invasive technique to determine the integrity of a pipe or quantitatively measure any corrosions or defects in the pipe. Non-destructive testing inspects and measures without doing harm to the pipe. There are many different ways of non-destructive testing, including, but not limited to, (a) acoustical emissions, (b) ultrasonic, (c) eddy current, (d) magnetic measurements, (e) microwave, (f) flux leakage or (g) x-ray. The use of x-rays or gamma rays is one of the more common techniques for non-destructive testing. In the use of x-ray or gamma ray technology for non-destructive testing, the pipe being tested is placed between the radiation source and a detector. The less radiation that reaches the detector, the better the pipe. The more radiation that reaches the detector, the more wear or corrosion in the pipe.

In industrialized countries such as the United States, many refineries or processing facilities were built years ago. Over time, corrosion or erosion can cause the pipes in the plant to wear thin and eventually leak. If a pipe leaks, depending upon what is being moved through the pipe, the leak can cause catastrophic results. The detection of a thin section of pipe before it leaks can be very critical.

The use of non-destructive testing for pipelines has become so common that standards have been developed by ASTM International. A collection of ASTM standards under "Radiology (X and Gamma) Method" have been developed.

One of the entities that has performed non-destructive testing on insulated pipes in the past is IHI Southwest Technologies, Inc. located in San Antonio, Tex., assignee of this invention. IHI has developed digital radiograph tools for detecting internal and external corrosion in insulated piping. Generally, a radiation source will create a radiation beam that penetrates a pipe under test. The radiation beam will penetrate not only the pipe, but also insulation there-around. A detector array is located on generally the opposing side of the pipe being inspected using a radiation source. In this manner, the detector array can determine if there is any corrosion and the severity of the corrosion. However, the prior systems developed by IHI were very complex and hard to move along a pipe being inspected to give good results. Also, dead zones would occur that were not being penetrated by the radiation. Because of the difficulty in installation and maneuverability of the prior digital radiographic imaging by IHI, it was difficult to eliminate the dead zones. The prior developed digital radiographic tool requires a lot of time to install and operate.

BRIEF SUMMARY OF THE INVENTION

It is an object of the present invention to provide for digital radiographic imaging of pipes.

It is another object of the present invention to provide a simplified, easy to use, structure for a digital radiograph tool that can be used for inspection of pipes.

It is yet another object of the present invention to provide a method and apparatus for using a digital radiograph tool for the inspection of pipes, particularly pipes that are insulated.

It is still another object of the present invention to provide an apparatus and method for the inspection of pipes using x-rays or gamma rays, which x-rays or gamma rays after passing through a pipe being inspected are detected and collected in a digital detector array. After processing the images received in the digital detector array, a determination of defects, location of defects, and severity of the defects is made.

A radiation source of x-rays or gamma rays is projected through a pipe under test. As the radiation source is moved along the pipe, a digital detector array is also moved along the pipeline, but on an opposing side from the radiation source. The amount of radiation that hits the digital detector array determines, after processing, if there is corrosion or other defects at predetermined points along the pipe. The more of the radiation signal that passes through the pipe, the greater the probability is of a defect in the pipe, such as corrosion. The stronger the signal reaching the digital detector array, the greater the probability of a defect.

The digital radiograph tool of the present invention has a track assembly attached to the pipe being inspected. On the track assembly is mounted a car assembly which has attached thereto an arm assembly. On the opposite end of the arm assembly is a linear digital array that is located adjacent to the pipe being inspected. Also connected to the car assembly is a collimator assembly which is located as close as possible to the opposing side of the pipe being tested from the linear digital array.

By making the arm assembly expandable and the collimator assembly adjustable, different size pipes can be accommodated. Also, the collimator assembly, track assembly, car assembly and linear digital array can be adjusted on the pipe as necessary to overcome obstructions that may be adjacent to (or touching) the pipe being inspected. By keeping the digital radiographic tool small and fully adjustable, it is much easier to inspect pipes with a minimum of cost and personnel.

BRIEF DESCRIPTION OF THE DRAWINGS

FIG. 5a is a top view of the track assembly.

FIG. 5b is an elevated side view of the track assembly.

FIG. 5c is a top view of separate sections of the track assembly.

FIG. 5d is an end view of FIG. 5a.

FIG. 6a is a perspective view of the car assembly.

FIG. 6b is an elevated side view of FIG. 6a.

FIG. 6c is a side view of FIG. 6a with the car body being separated from the linear bearing chassis.

FIG. 6d is an end view of FIG. 6a, but with the removable pins removed.

FIG. 6e is an exploded side view of FIG. 6a.

FIG. 7b is a side view of FIG. 7a.

FIG. 7c is the opposite end view of the fully collapsed arm assembly from the one shown in FIG. 7a.

DESCRIPTION OF THE PREFERRED EMBODIMENT

Figure 1:
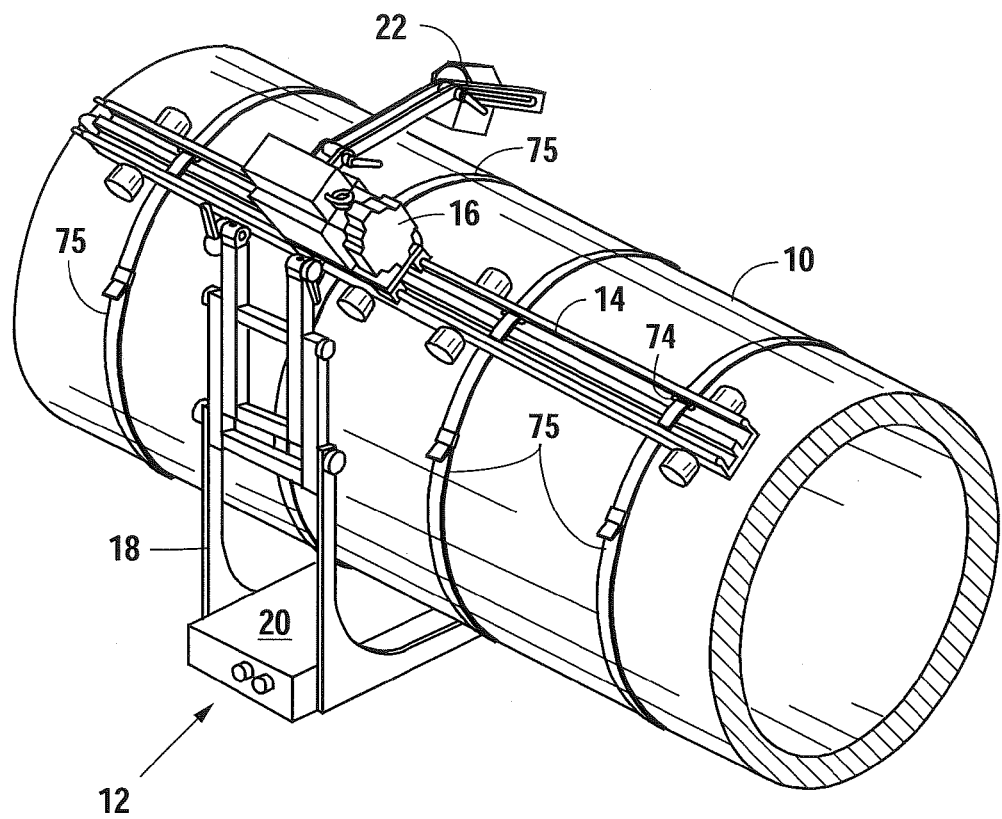
FIG. 1 is a perspective view of a digital radiographic tool made according to the present invention being used to inspect a pipe.
Figure 2:
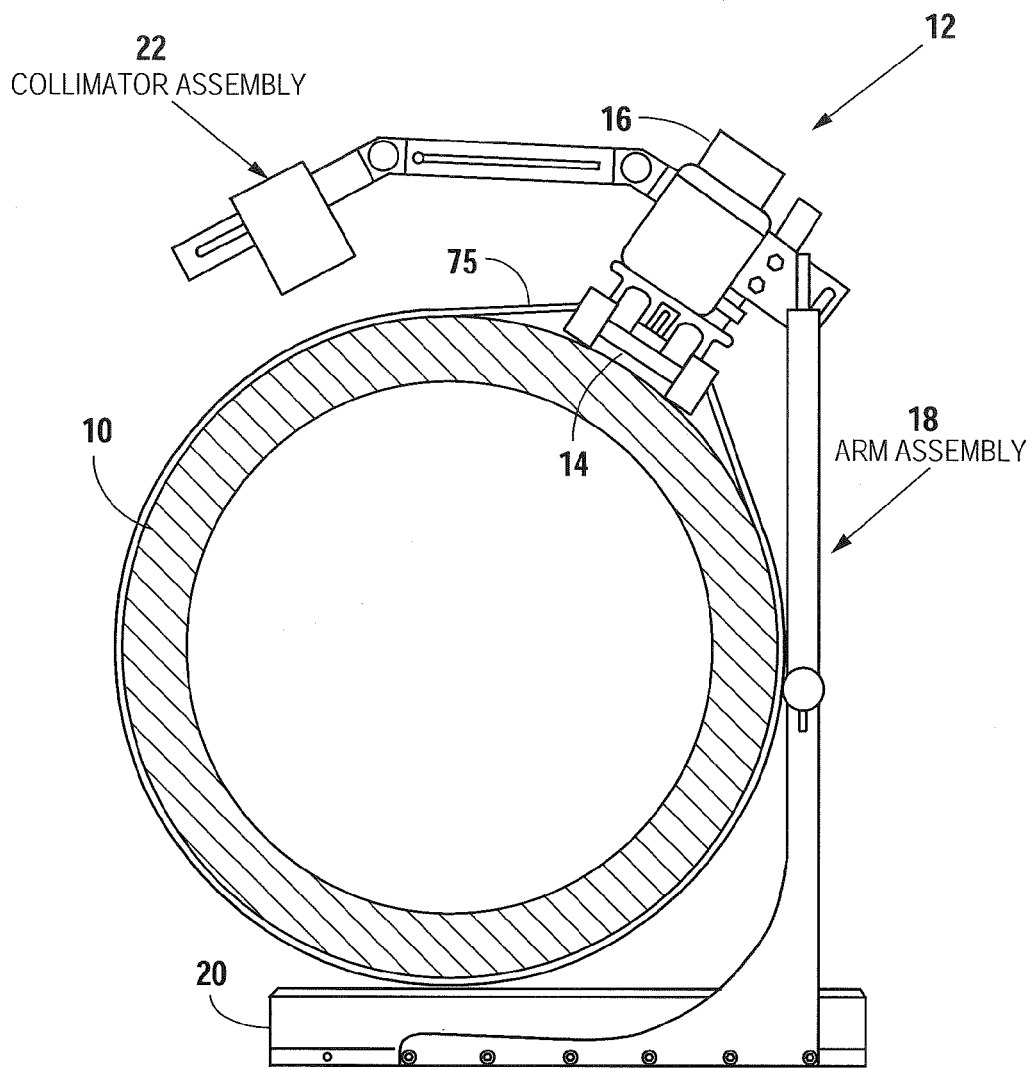
FIG. 2 is a left end view of FIG. 1.
Figure 3:
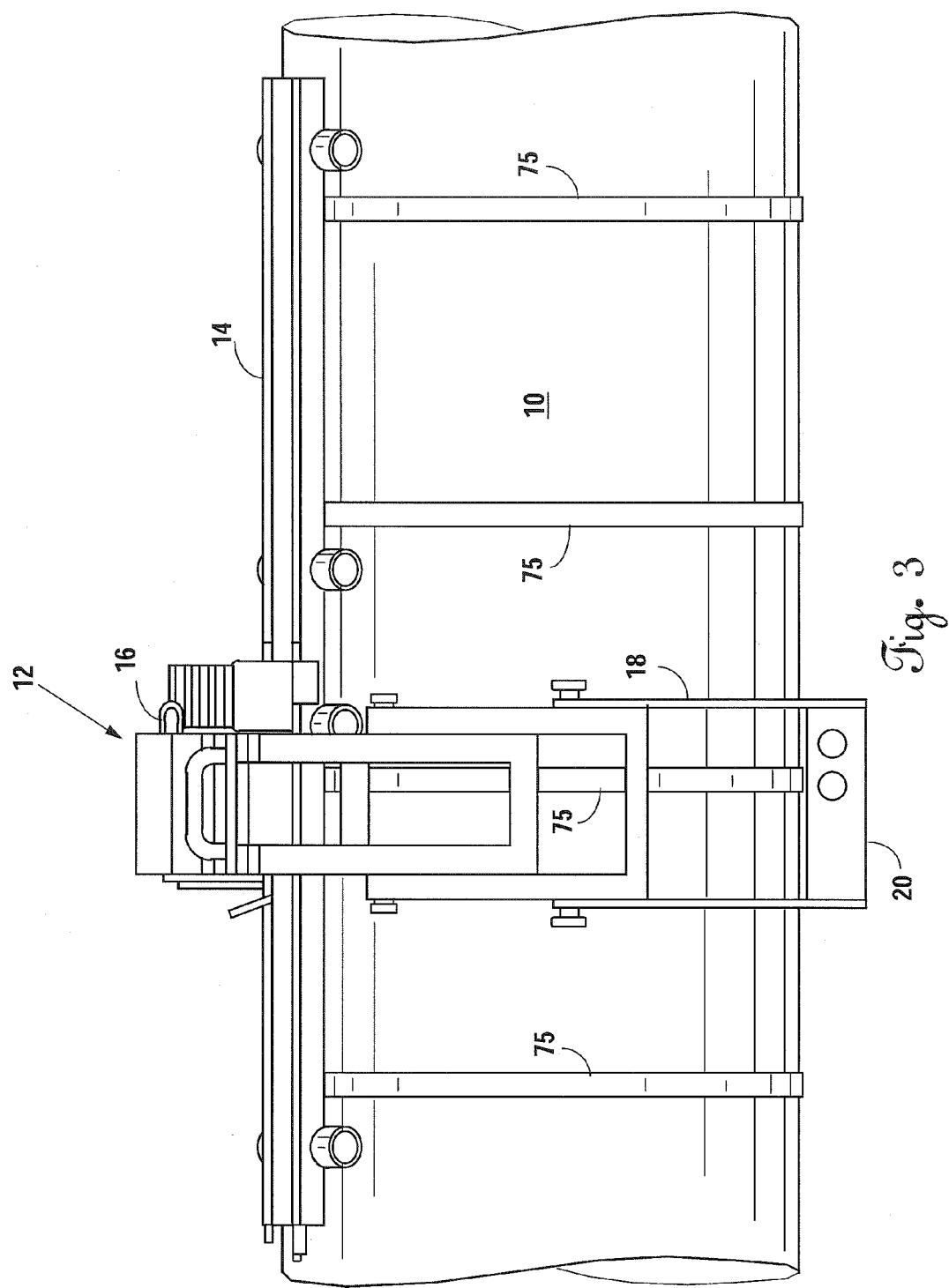
FIG. 3 is an elevated side view of FIG. 1.

Referring now to FIGS. 1, 2 and 3 in combination, a pipe 10 is being inspected by a digital radiographic tool 12. The digital radiographic tool 12 has a track assembly 14 with a drive car 16 mounted thereon. The drive car 16 can move back and forth along the track assembly 14.

Attached to one side of the drive car 16 is an arm assembly 18. On the distal end of the arm assembly 18 is mounted a linear digital array 20. On the opposite side of the drive car 16 from the arm assembly 18 is attached the collimator assembly 22.

The drive car 16 of the digital radiographic tool 12 moves back and forth along pipe 10 on the track assembly 14. As the drive car 16 moves back and forth, it carries the collimator assembly 22 which generates x-rays or gamma rays projected towards the pipe 10. On the opposite side of the pipe 10 from the collimator assembly 22, the x-rays or gamma rays are collected in the linear digital array 20.

Figure 4:
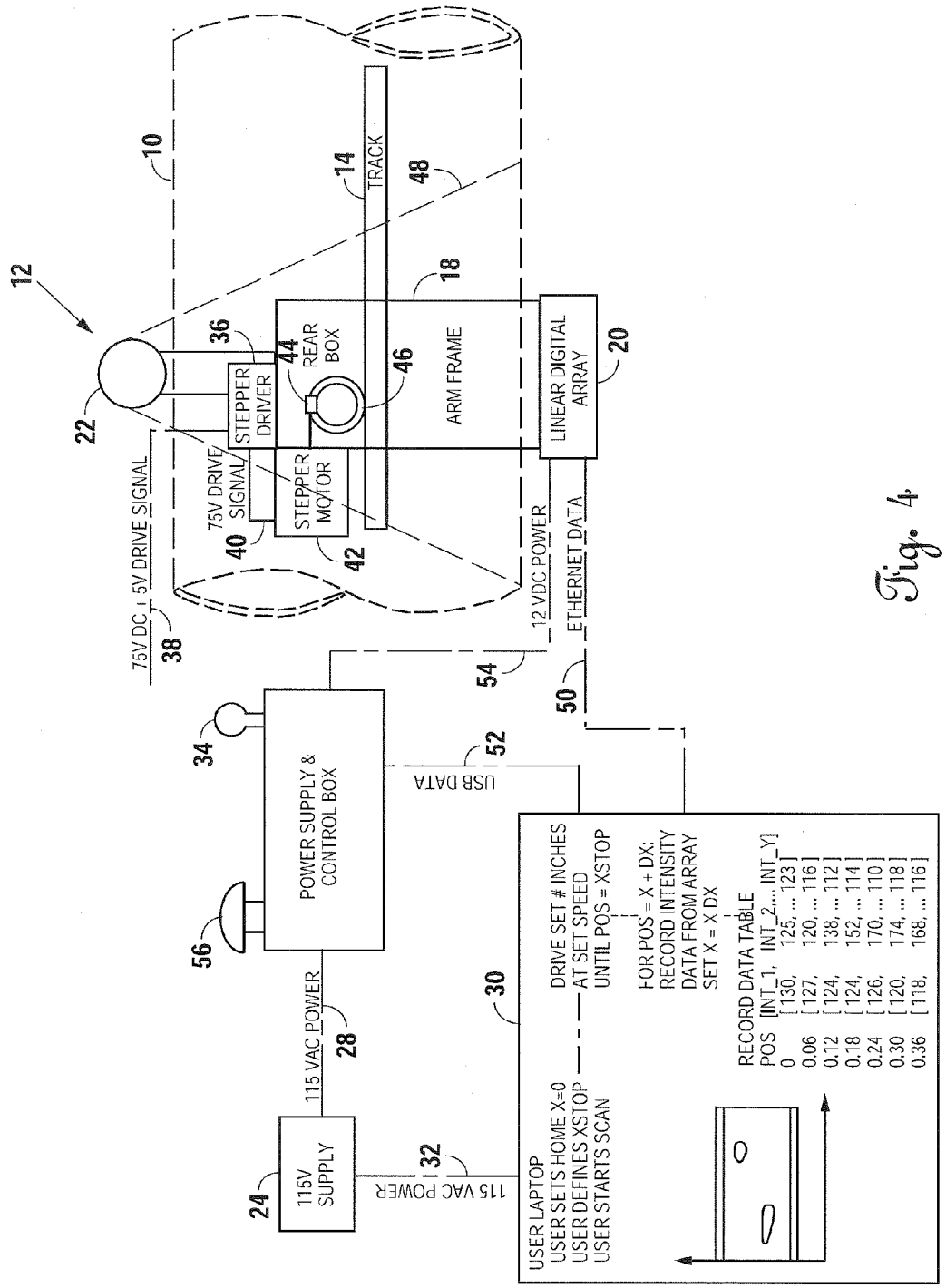
FIG. 4 is a block diagram of the electronic controls of the digital radiographic tool illustrated in FIG. 1.
Figure 6E:
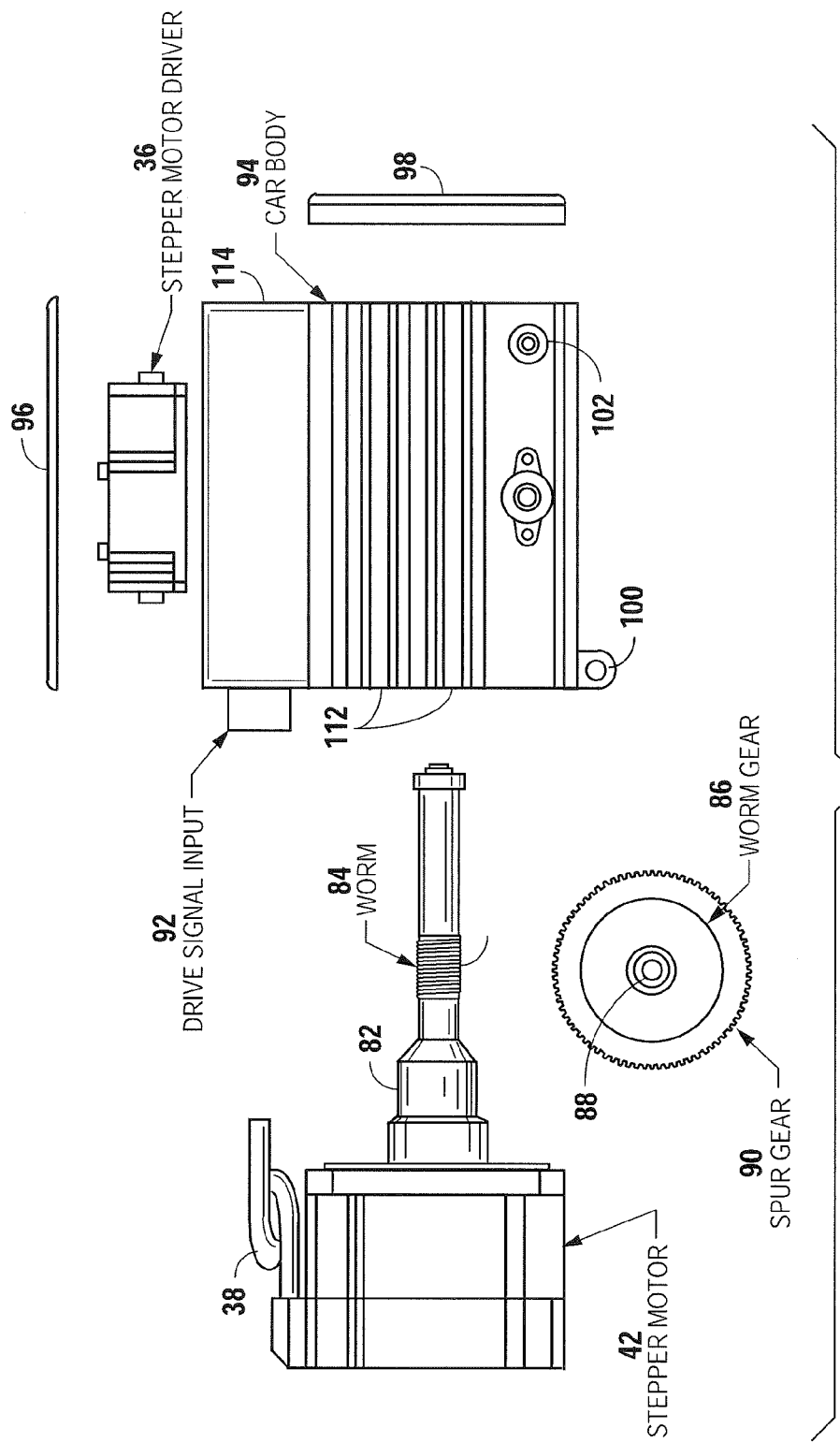

Referring now to FIG. 4, a pictorial block diagram of the pipe 10 being inspected by a digital radiographic tool 12 is shown. The digital radiographic tool 12 includes the arm assembly 18 and the collimator assembly 22.

Power is supplied to the digital radiographic tool 12 by 115V power supply 24 which connects to a power supply and control box 26 via 115 VAC power line 28. Simultaneously, the 115V power supply 24 supplies power to a user laptop 30 via power line 32.

The power supply and control box 26 has a joy stick 34 connected to a stepper motor 36 within the drive car 16 (see FIGS. 1, 2 and 3) via drive signal connection 38. The stepper motor 36 provides a 75V drive signal 40 to stepper motor 42. The stepper motor 42 through a gear box 44 drives gears 46 that mechanically connect with track assembly 14.

As the drive car 16 (see FIGS. 1, 2 and 3) is driven along track 14, the collimator assembly 22 emits x-rays (or gamma rays) 48 which penetrate pipe 10. The x-rays 48 that penetrate the pipe 10 are then collected by the linear digital array 20. The signals collected by the linear digital array 20 are fed via Ethernet data connection 50 to the user laptop 30. From the laptop 30, USB data connection 52 connects to power supply and control box 26. Also, the linear digital array 20 receives its power from power supply and control box 26 via power connection 54.

While many different types of software can be used, Applicants have found that iX-Control by Shaw Pipeline Systems to be a good software to use. Using the iX-Control software, the user laptop 30 can give the commands to the power supply and control box 26 to move the digital radiographic tool 12 a certain distance along pipe 10 and it will occur. By having the collimator assembly 22 emit x-rays 48 as the digital radiographic tool 12 is moved along the track assembly 14, radiated signals will be detected by the linear digital array 20. The user, through the user laptop 30, will set the start point to determine the distance of movement and speed while recording data. The recorded data will indicate whether pipe 10 does (or does not) have defects therein such as would be caused by corrosion. Even if the pipe 10 is surrounded by insulation, the x-rays 48 will penetrate the insulation and the pipe 10 sufficient to give a table recording or a pictorial recording as illustrated in the user laptop 30. If an emergency stop is necessary, an emergency stop button 56 is provided on the power supply and control box 26.

Referring now to FIGS. 5(a), (b), (c) and (d), the track assembly 14 will be explained in more detail. Track assembly 14 is made up of modular sections 58 and 60 (see FIG. 5c). As many more sections as may be necessary can be used. Applicants have found that section links of 2 ft. and/or 4 ft. to be ideal. The modular sections 58 and 60 are aligned by alignment pins 62 at each end of the linear rails 64. Opposing ends of the linear rail 64 from the alignment pins 62 have holes therein (not shown) to receive the alignment pins 62. The modular sections 58 and 60 are held together by latch 66.

The linear rails 64 are mounted on a track frame 68. Contained within the track frame 68 is a gear rack 70 for meshing with a gear as will be subsequently described. On each end of the modular sections 58 and 60 are located idle roller wheels 72. The idle roller wheels 72 may be held on the track frame 68 by any conventional means such as by bearings and axles. Each of the modular sections 58 and/or 60 are held to the pipe 20 by tie-downs 75 that extend through tie-down slots 74 and around pipe 10 (see FIGS. 1-4).

Figure 9:
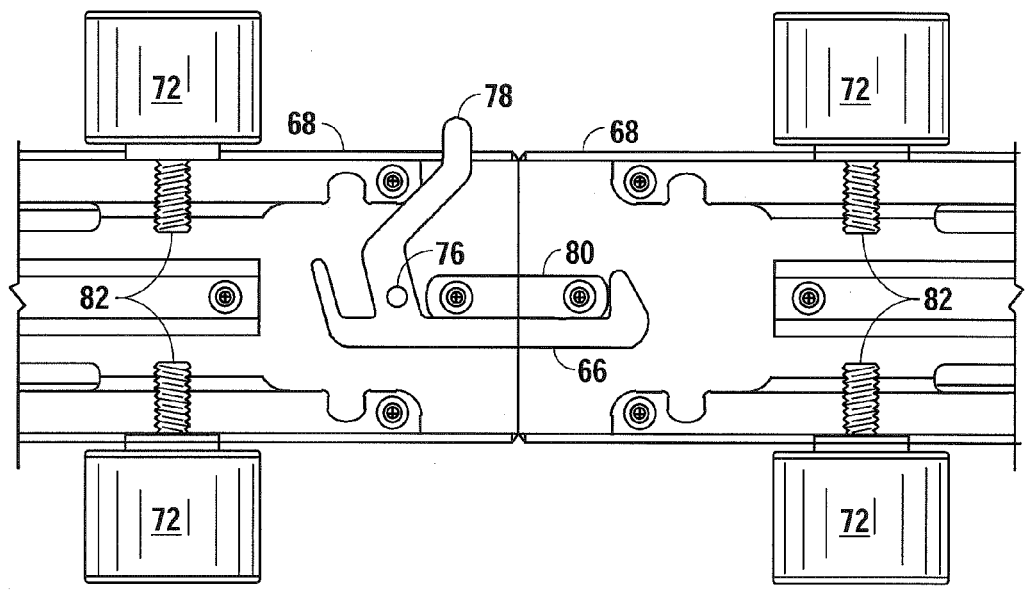
FIG. 9 is a bottom sectional view of two tracks of the track assembly connected together.

Referring now to FIG. 9 in conjunction with FIGS. 5(a), (b), (c) and (d), a bottom view with the latch 66 is illustrated. FIG. 9 is a cross-sectional view of FIG. 5(b) along section lines 9-9. The latch 66 is pivotally mounted on pivot pin 76. If a user presses release button 78, the latch 66 will be pivoted about pivot pin 76 so that it disengages from latch stop 80. The idle roller wheels 72 are shown threadably connected to the track frame 68 by wheel screws 82.

Referring now to FIGS. 6(a)-(e), the drive car 16 will be discussed in detail. The drive car 16 has a stepper motor 42 that connects through a coupler 82 to drive the worm 84 that will mesh with worm gear 86 (see FIG. 6e). The worm gear 86 is connected by drive shaft 88 to the spur gear 90. Spur gear 90 meshes with the gear rack 70 (shown in FIGS. 5(a), (c) and (d)) to drive the entire drive car 16. Power for the stepper motor 42 is received through the drive signal connection 38 connecting through the drive signal input 92.

Attached to the top of the car body 94 is the stepper motor driver 36. A waterproof cover 96 seals the stepper motor driver 36 inside of car body 94. Front cap 98 enclosed the front of car body 94. Pin holes 100 and 102 extend through car body 94 to receive removable pins 104 and 106, respectively, there through. Removable pin 104 and 106 are spring-loaded to be removed upon pushing end buttons 108 or 110, respectively (see FIGS. 6d and 6e).

T-slots 112 are formed on both sides and in the top of the car body 94. The T-slots 112 allow T-bolts (not shown) to be inserted therein on which items can be attached to the drive car 16. For example, the stepper motor driver 36 is contained in stepper motor driver housing 114 by means of T-slots 112 in the car body 94, which T-slots are located directly below the stepper motor driver housing 114.

Referring to FIG. 6c, a linear bearing chassis 116 is shown disconnected and below from the car body 94. The linear bearing chassis 116 is connected to the car body 94 by removable pins 104 and 106 extending through pin holes 100 and 102, respectively (see FIG. 6d). The spur gear 90 extends below the drive car 16 as is illustrated in FIG. 6b. Hence, the spur gear 90 meshes with the gear rack 70 of the track assembly as shown in FIGS. 5a, c and d.

The bottom of the linear bearing chassis 66 has linear bearings 118 mounted there below. The linear bearings 118 receive the linear rails 64 (see FIGS. 5a, b, c and d and FIG. 6d) therein. To reduce friction between the linear bearings 118 and the linear rail 64, the linear bearings 118 have bearing liners 120 therein.

Figure 7A:
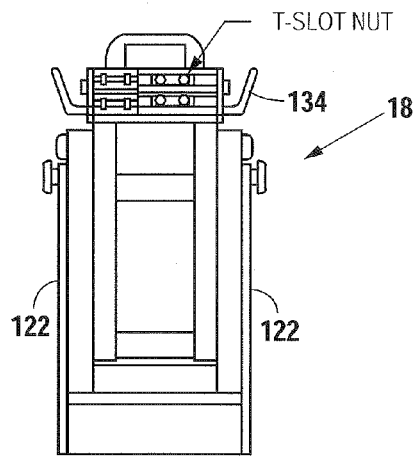
FIG. 7a is an end view of the fully collapsed arm assembly.
Figure 7B:
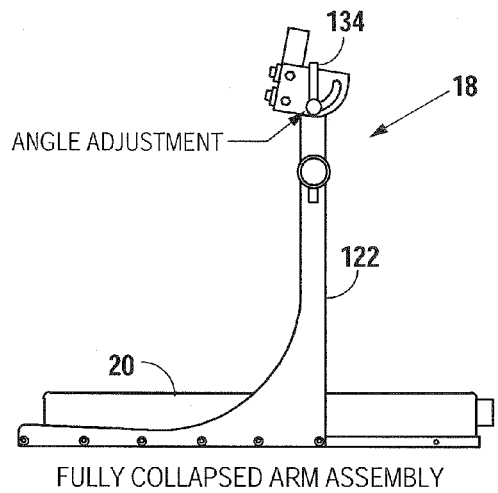
Figure 7C:
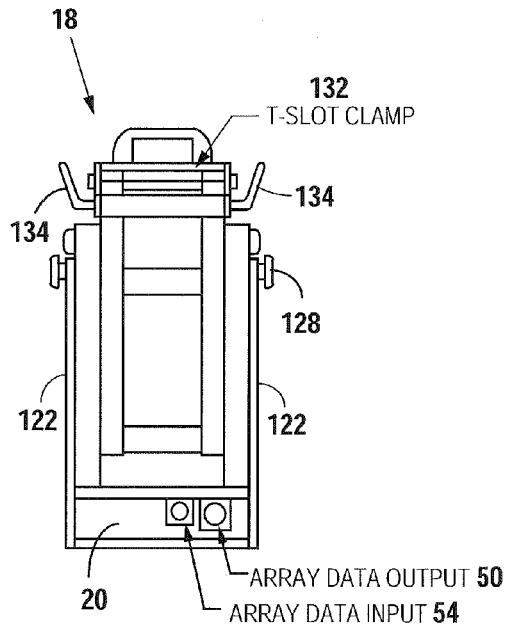
Figure 7D:
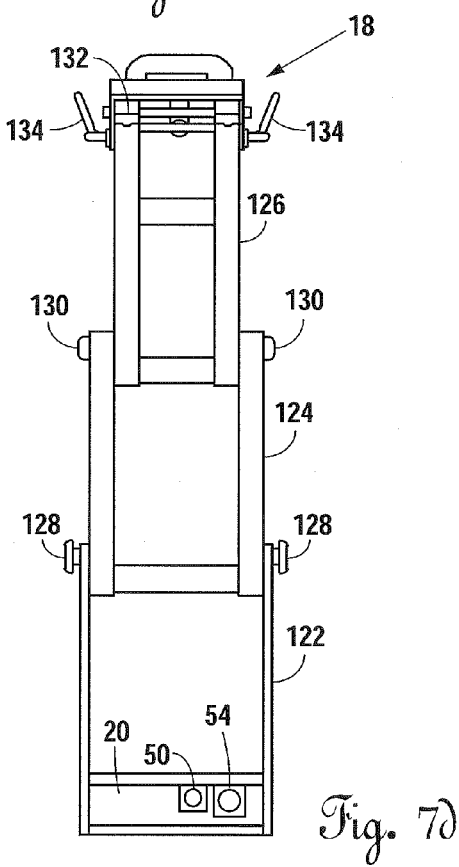
FIG. 7d is the same view as FIG. 7c, but with the arm assembly fully extended.

Referring now to FIGS. 7a-d, the arm assembly 18 is shown in more detail. The arm assembly 18 has a radial arm plate 122 on either side thereof. In FIGS. 7a, b and c, the arm assembly 18 is fully collapsed. In FIG. 8d, the arm assembly 18 is fully extended with an intermediate telescoping T-slot frame 124 and an upper telescoping T-slot frame 126. The intermediate telescoping T-slot frame 124 is held in position by thumb screws 128. The upper telescoping T-slot frame 126 is held in position by thumb screws 130. On the upper end of the arm assembly 18, a T-slot clamp 132 may be pivoted by loosening clamping L-handles 134. By loosening clamping L-handles 134, the T-slot clamp 132 may be pivotally adjusted (see FIG. 7b).

At the bottom of the arm assembly 18 and mounted between radial arm plates 122 is the linear digital array 20. The linear digital array 20 has an Ethernet data connection 50 and a power connection 54.

Figures 8A, 8B:
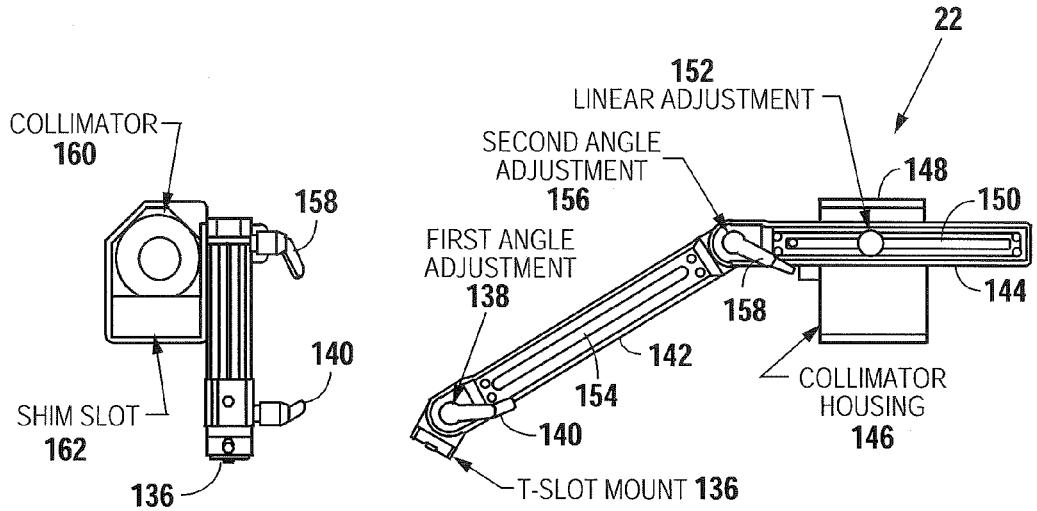
FIG. 8a is an end view of a collimator assembly.
FIG. 8b is a side view of the collimator assembly.

Connected in the T-slot clamp 134 is the T-slot mount 136 of the collimator assembly 22 (see FIGS. 8a and b). The first angle adjustment 138 of the collimator assembly 22 is provided by loosening clamping L-handle 140. Held in position by first clamping L-handle 140 is a first collimator arm 142 and a second collimator arm 144, on either of which can be mounted collimator housing 146. Thumb screw 148 secures the collimator housing via slot 150 on the second collimator arm 144. The thumb screw 148 allows for linear adjustment 152 of the collimator housing 146. Also, the collimator housing 146 could be mounted in slot 154 of first collimator arm 142.

A second angle adjustment 156 is provided between first collimator arm 142 and second collimator arm 144 by a second clamping L-handle 158. Inside of the collimator housing 146 is located the collimator 160. A shim slot 162 is also provided if minor adjustments to the collimator 160 need to be made.

By use of the arm assembly 18 as described in FIGS. 7a-d and the collimator assembly 22 as described in FIGS. 8a and b, the adjustability of the digital radiographic tool 12 is illustrated. This adjustability feature allows either the collimator 160 or the linear digital array 20 to be adjusted to reach under and/or around pipe supports. Due to the adjustability features, various diameter pipes can be accommodated. The adjustability features of the digital radiographic tool 12 allow a single person to operate the tool and to inspect a greater percentage of the pipe than prior inspection devices.

Figure 10:
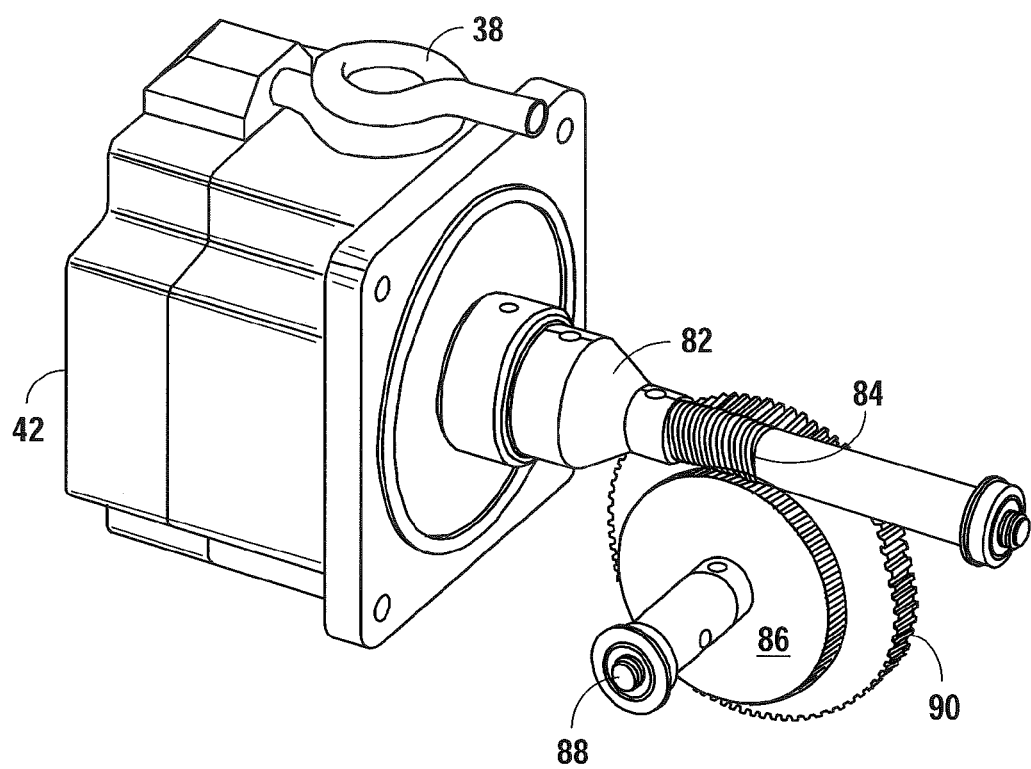
FIG. 10 is a perspective view of the stepper motor illustrating the gear connections thereto.

Referring now to FIG. 10, connection of the stepper motor 42 through coupler 82 to the worm 84 is illustrated in more detail. The worm 84 meshes with the worm gear 86 mounted on drive shaft 88. As the worm 84 turns, the worm gear 86 also turns and rotates drive shaft 88 on which spur gear 90 is also mounted. The turning of the spur gear 90 which meshes with the gear rack 70 (see FIG. 2), moves the drive car 16 and the entire digital radiographic tool 12 along the track assembly 14.

What we claim is:

1. A digital radiographic tool for inspecting a pipe with obstructions adjacent said pipe, a power source to operate said digital radiographic tool, said digital radiographic tool comprising:
    a track assembly removably secured along said pipe, said track assembly being in sections joined and held together by a latch;
    a gear rack in said track assembly and extending along with said track assembly;
    a drive car mounted on said track assembly;
    an arm assembly attached on a first end to said drive car, which arm assembly is perpendicular and adjacent to said pipe, said arm assembly being extendable along a longitudinal axis thereof;
    a linear digital array being attached to a second end of said arm assembly and held adjacent said pipe;
    a collimator assembly attached to said drive car on a near end thereof;
    a collimator on a far end of said collimator assembly, said collimator for directing x-rays on gamma rays toward said pipe, said linear digital array for collecting x-rays or gamma rays that pass through said pipe;
    gears in said drive car connected to said gear rack in said track assembly;
    a motor in said drive car for turning said gears, said power source being connected to said motor, said collimator and said linear digital array so that as said drive car is moved along said track assembly by said motor via said gears, said collimator directs said x-rays or gamma rays toward said pipe and said linear digital array collects any x-rays or gamma rays that have passed through said pipe; and
    recorder for receiving and recording said collected x-rays or gamma rays verses position along said pipe to show any defects in said pipe.

2. The digital radiographic tool for inspecting a pipe with obstructions adjacent said pipe as recited in claim 1 wherein said arm assembly is adjustable in length and said collimator assembly is pivotally connected to said drive car so that said digital radiographic tool can inspect pipes of different diameters.

3. The digital radiographic tool for inspecting a pipe with obstructions adjacent said pipe as recited in claim 2 wherein said collimator is adjustable along said collimator assembly and said collimator assembly has multiple pivot points, thereby allowing said digital radiographic tool to be adjusted in multiple ways to avoid said obstructions adjacent said pipe.

4. The digital radiographic tool for inspecting a pipe with obstructions adjacent said pipe as recited in claim 1 wherein said motor is a stepper motor with a stepper driver to move said digital radiographic tool a predetermined distance along said pipe with each drive signal received.

5. The digital radiographic tool for inspecting a pipe with obstructions adjacent said pipe as recited in claim 4 further includes a control for sending said drive signal to said stepper motor, said control being connected to said recorder to show said defects in said pipe.

6. The digital radiographic tool for inspecting a pipe with obstructions adjacent said pipe as recited in claim 5 wherein said control includes a laptop computer programmed to operate said digital radiographic tool and show said defects in said pipe.

7. The digital radiographic tool for inspecting a pipe with obstructions adjacent said pipe as recited in claim 1 wherein said arm assembly has multiple T-slot frames telescopingly connected together and held in a desired position by thumb screws.

8. The digital radiographic tool for inspecting a pipe with obstructions adjacent said pipe as recited in claim 7 wherein said track assembly has a track frame with linear rails attached on either side of said track frame, said gear rack being between said linear rails.

9. The digital radiographic tool for inspecting a pipe with obstructions adjacent said pipe as recited in claim 8 wherein said sections of said track assembly has on opposite ends of said linear rails alignment pins and alignment holes for mating together.

10. The digital radiographic tool for inspecting a pipe with obstructions adjacent said pipe as recited in claim 9 wherein said latch is pivotally mounted on one end of said section of said track frame, said latch removably connecting with a catch on an opposite end of a next of said sections of said track frame.

11. The digital radiographic tool for inspecting a pipe with obstructions adjacent said pipe as recited in claim 1 wherein said drive car has a car body with multiple T-slots therein, said T-slots being used to attach said arm assembly and said collimator assembly thereto.

12. The digital radiographic tool for inspecting a pipe with obstructions adjacent said pipe as recited in claim 11 wherein said motor is a stepper motor, linear bearings are attached to a linear bearing chassis, said linear bearing chassis being secured underneath said car body, said linear bearings allowing said drive car to move along linear rails in said track assembly.

13. The digital radiographic tool for inspecting a pipe with obstructions adjacent said pipe as recited in claim 11 wherein said gears include a screw gear mating with a worm gear turned by said stepper motor, said screw gear turning a spur gear that mates with said gear rack to move said digital radiographic tool.

14. The method for inspecting the pipe for defects as recited in claim 1 includes a further step of inspecting adjacent said obstructions by said using said first adjusting step and said second adjusting step to inspect around said obstructions.

15. The method for inspecting the pipe for defects as recited in claim 14 wherein said drive car has T-slots on sides thereof, said first attaching and said third attaching steps using T-bolts secured in said T-slots.

16. The method for inspecting the pipe for defects as recited in claim 15 wherein said drive car includes linear bearings thereunder and said track assembly has parallel tracks, said clipping step includes said linear bearings clipping onto said parallel tracks.

17. The method for inspecting the pipe for defects as recited in claim 14 wherein said gears of said drive car include a worm turning a worm gear, which worm gear turns a spur gear meshed with said gear rack.

18. The method for inspecting the pipe for defects as recited in claim 14 wherein said latching step has a pivotally mounted latch engaging a latch catch between adjacent sections of said track assembly, a release button for said latch extending to a side of said track assembly.

19. The method for inspecting the pipe for defects as recited in claim 16 wherein said parallel tracks have pins and pin holes on opposite ends of each section of said track assembly so that said pins mate with said pin holes during said latching step.

20. A method for inspecting a pipe for utilizing a power source to detect defects in said pipe, which said pipe has obstacles adjacent thereto, said method including the following steps:

mounting sections of a track assembly longitudinally along said pipe;

latching together said sections of said track assembly;

clipping a drive car on said track assembly;

first attaching an arm assembly on a first end to said drive car, said arm assembly being perpendicular and adjacent to said pipe;

second attaching a second end of said arm assembly to a linear digital array, said linear digital array being held adjacent said pipe;

third attaching a near end of a collimator assembly to said drive car;

securing a collimator on said collimator assembly near a far end thereof, first adjusting length of said arm assembly to slightly exceed diameter of said pipe;

second adjusting angle of said arm assembly and said collimator assembly with respect to said pipe so that said collimator can project x-rays or gamma rays against a side of said pipe and said linear digital array can collect x-rays or gamma rays that have passed through said pipe;

meshing gears in said drive car with a gear rack in said track assembly;

connecting said power source to said drive car, said collimator, said linear digital array and a collimator;

driving said drive car along said track assembly with a stepper motor in said drive car turning said gears while simultaneously, said collimator projects said rays on said pipe and said linear digital array collects said rays that have passed through said pipe; and processing said collected rays and distance traveled by said drive car in said computer to locate any defects in said pipe.

* * * * *